United States Patent [19]

Sawyer et al.

[11] Patent Number: 5,307,372
[45] Date of Patent: Apr. 26, 1994

[54] RADIO TRANSCEIVER FOR TRANSMITTING AND RECEIVING DATA PACKETS

[75] Inventors: Jonathan F. Sawyer, Golden; Dennis J. Gardner, Louisville, both of Colo.

[73] Assignee: CliniCom Incorporated, Boulder, Colo.

[21] Appl. No.: 990,568

[22] Filed: Dec. 15, 1992

Related U.S. Application Data

[63] Continuation-in-part of Ser. No. 652,976, Feb. 8, 1991, Pat. No. 5,179,569.

[51] Int. Cl.$^5$ .................................... H04L 27/30
[52] U.S. Cl. ............................ 375/1; 380/34; 340/573; 340/600; 340/870.03; 340/870.11; 340/870.18; 340/870.28
[58] Field of Search ............. 375/1; 380/34; 342/37, 342/45, 50; 340/505, 539, 540, 573, 600, 870.03, 870.11–870.14, 870.18, 870.28

[56] References Cited

U.S. PATENT DOCUMENTS

| | | | |
|---|---|---|---|
| 2,864,943 | 12/1958 | Schultz | 342/50 |
| 3,949,397 | 4/1976 | Wagner et al. | 342/45 |
| 4,042,906 | 8/1977 | Ezell | 340/870.13 X |
| 4,601,043 | 7/1986 | Hardt et al. | 375/1 |
| 4,653,068 | 3/1987 | Kadin | 375/1 |
| 4,724,435 | 2/1988 | Moses et al. | 340/870.13 |

Primary Examiner—Bernarr E. Gregory
Attorney, Agent, or Firm—Beaton & Swanson

[57] ABSTRACT

An apparatus for transmitting and receiving packets of data among a multitude of base and remote units utilizing a frequency hopping technique. The apparatus uses a single clock source for synchronizing the analog signal processing circuit, the modular encoder and the micrprocessor, and uses an inexpensive microprocessor with a serial peripheral interface.

14 Claims, 1 Drawing Sheet

RADIO TRANSCEIVER FOR TRANSMITTING AND RECEIVING DATA PACKETS

This is a continuation-in-part of Ser. No. 07/652,976 filed Feb. 8, 1991, now U.S. Pat. No. 5,179,569.

BACKGROUND OF THE INVENTION

The present invention relates to an apparatus for operating a radio communication system which is especially suited for transmission of small packets of data among a multitude of base and remote units utilizing a frequency hopping technique to minimize interference from external sources and among internal units.

The invention has particular, but not exclusive, utility in the health care environment. The invention allows for the identification of patients and patient-related items, and provides for quick and accurate updating of patient medical and accounting records.

Medical institutions are faced with a competitive environment in which they must improve profitability and yet simultaneously improve patient care. There are several factors which contribute to the ever increasing costs of hospital care. For example, there is an ever increasing amount of paperwork required by nurses, pharmacists and laboratory personnel. In addition, inaccurate recording of drugs, supplies and tests involved in patient care results in decreasing revenues by a failure to fully capture billing opportunities of these actual costs. Inadequate management also results in a failure to provide an accurate report of all costs involved in treating a particular illness. The lack of accurate and rapid transfer of patient information often reduces the accuracy or effectiveness of drug administration and patient care, thereby increasing the duration of hospital stay.

In addition, hospitals and other institutions must continuously strive to provide quality patient care. Medical errors, where the wrong patient receives the wrong drug at the wrong time, in the wrong dosage or even the wrong surgery, are a significant problem for all health care facilities. Many prescription drugs and injections are identified merely by slips of paper on which the patient's name and identification number have been handwritten by a nurse or technician who is to administer the treatment. For a variety of reasons, such as the transfer of patients to different beds and errors in marking the slips of paper, a patient may be given an incorrect treatment. Further, as health care facilities continue to decrease the number of staff personnel as a cost cutting measure, the possibility of personnel errors will most likely increase.

Some of these problems have been addressed in U.S. Pat. No. 4,850,009 by Zook, assigned to the assignee of the present invention. The Zook patent describes a portable handheld terminal which includes a data-entry keyboard, a data-entry optical bar code reader and an RF transceiver. The bar code reader and the keyboard can be used to enter data regarding the patient identity, the type of drug to be administered or other information. The information is transmitted to a base transceiver which modulates the information and electronically communicates with a central recordation means such as a CPU. The base transceiver can transmit verifications or other limited information received from the CPU back to the portable handheld terminal. A set of terminals can also be in hard wire electronic communication with the CPU to enter and display data such as billing information. While the system described in the Zook patent is very effective, it is limited by the number of available non-interfering RF channels.

Some attempt has been made to overcome the inherent limitations of radio communications by utilizing spread spectrum technology. In spread spectrum systems, the radio signal is transmitted over a relatively broad band. This results in a lower power per bandwidth (W/Hz) but a broad channel. The low power at any given frequency within the channel lessens the potential for the system to interfere with other systems. At the same time, the broad channel allows a fairly large throughput rate.

The Federal Communications Commission ("FCC") has set aside certain radio frequency bands for low power communications devices using spread spectrum modulation. Current FCC regulations allow spread spectrum technology in the bands of 902-928 MHz, 2400-2483.5 MHz and 5725-5850 MHz. Because components are not readily available in the later two bands, most systems now in use are designed for operation in the 902-928 band. The FCC regulations require no site license but limit power to 1 watt.

The most common spread spectrum systems employ direct sequencing methods, in which a signal is spread over a relatively broad band with the hope that frequency-specific interference will be overcome by clear transmissions elsewhere in the broad band. Direct sequencing methods have the advantage of relatively high throughput rates and low external interference problems. However, they use up a broad band, suffer from near-far problems and must have short range to keep under the FCC power limitations. The use of multiple channels can address the near-far problems, but at the cost of increased external interference problems, since each of the multiple channels is then a narrower band. When direct sequencing methods are used with multiple remote transceivers, it is generally necessary to utilize some form of carrier sensing multiple access ("CSMA") technique, in which each remote transceiver queues up to wait for an opening in the base transceiver. Therefore, while the overall transmission rate may be relatively high, the acknowledgement times may be unacceptably slow as the queued up remote units wait their turn for communication with the base transceiver.

Another spread spectrum technology is known as frequency hopping. In frequency hopping, the signal is in a relatively narrow channel as in conventional radio communication, but the channel hops among a predetermined set of frequencies within the spread spectrum. The FCC rules specify various permissible operating parameters for spread spectrum communications using the designated frequency bands such as the rate of frequency hopping and the frequency width and separation. As compared to direct sequencing, frequency hopping has the potential for longer range transmissions (since the limited power is not spread over a broad band) but presents some problems with fast synthesizers and synchronization requirements. Both systems tend to limit frequency specific external interference but in different ways; direct sequencing systems limit frequency specific external interference by spreading the signal over a wide band, while frequency hopping systems limit frequency specific external interference by hopping to a new, interference-free channel periodically. For purposes of the present invention, one of the most important differences is that dividing the spread spectrum into a large number of frequency hopping channels rather than a lesser number of direct sequencing channels results in fairly low throughput per channel but also results in a large number of non-interfering channels. Therefore, the overall throughput can still be high. Moreover, the acknowledgement times are very fast, because at any given time at least one of the large number of channels is likely to be available. This tradeoff between throughput rates per channel and channel availability favors frequency hopping for applications with a large number of simultaneous transmissions of small information packets, and favors direct sequencing for applications with a small number of simultaneous transmissions of large information packets.

A frequency hopping technique is described in U.S. Pat. No. 4,850,036 by Smith for use with two-way communication links. Smith uses a fairly slow frequency hopping rate and is limited in its application by parameters that are optimized for two-way voice communication rather than data transmission. In particular, the transmission channel and reception channel are different in order to accommodate the two-way voice communication. Also, the Smith system contemplates remote units being locked to a given control unit without any capacity to choose the best signal from among physically separated control units.

SUMMARY OF THE INVENTION

The present invention provides an interactive computer link between a mainframe computer system and a large number of remote portable terminals, using RF spread spectrum frequency hopping. The operating parameters are deliberately chosen transmitting small data packets requiring fast acknowledgement speeds. The RF transmissions within an area of potential interference are generally on different channels, and the transmissions hop from channel to channel in a predetermined synchronous sequence, thereby minimizing both internal interference and external interference.

The system of the present invention is preferably used with a plurality of base transceivers and a plurality of remote transceivers within a NODE. Within each NODE, the base transceivers and remote transceivers are synchronized and a predetermined frequency hopping sequence is utilized. Preferably, the predetermined frequency hopping sequence is unique among the NODES in a geographic area of potential interference, and each base transceiver within a NODE is at a unique point in the frequency hopping sequence, so that no two base transceivers in a NODE are on the same channel at the same time.

Each base transceiver transmits a calling signal on designated calling frequencies within the frequency hopping sequence. Each remote transceiver monitors the calling signals to establish a preferred base transceiver list. When the remote transceiver is in use, it draws from the preferred base transceiver list and transmits and receives at the point in the frequency hopping sequence corresponding to the point at which the base transceiver in the preferred list is transmitting, and then hops through the frequency hopping sequence with that base transceiver.

The transceivers of the preferred embodiment include transmitting and receiving circuits including a phase lock loop, a microprocessor and a modular transmitting and receiving circuits and the microprocessor, thereby avoiding the need for more than one expensive clock. The microprocessor is an inexpensive unit with a serial peripheral interface having a shift register, a read buffer and a high speed data bus. Data is accumulated in the shift register and transferred to the data bus a byte at a time. The transmission of predetermined bit sequences is used to synchronize units with one another. The DC and low frequency components of the transmissions are minimized by use of a dual binary code containing a +1, a−1 and a 0.

The system has very short acknowledgement times and a very fast frequency hopping sequence. The system is especially suited to transmitting and receiving small data packets.

DETAILED DESCRIPTION OF THE PREFERRED EMBODIMENTS

Figure 1:
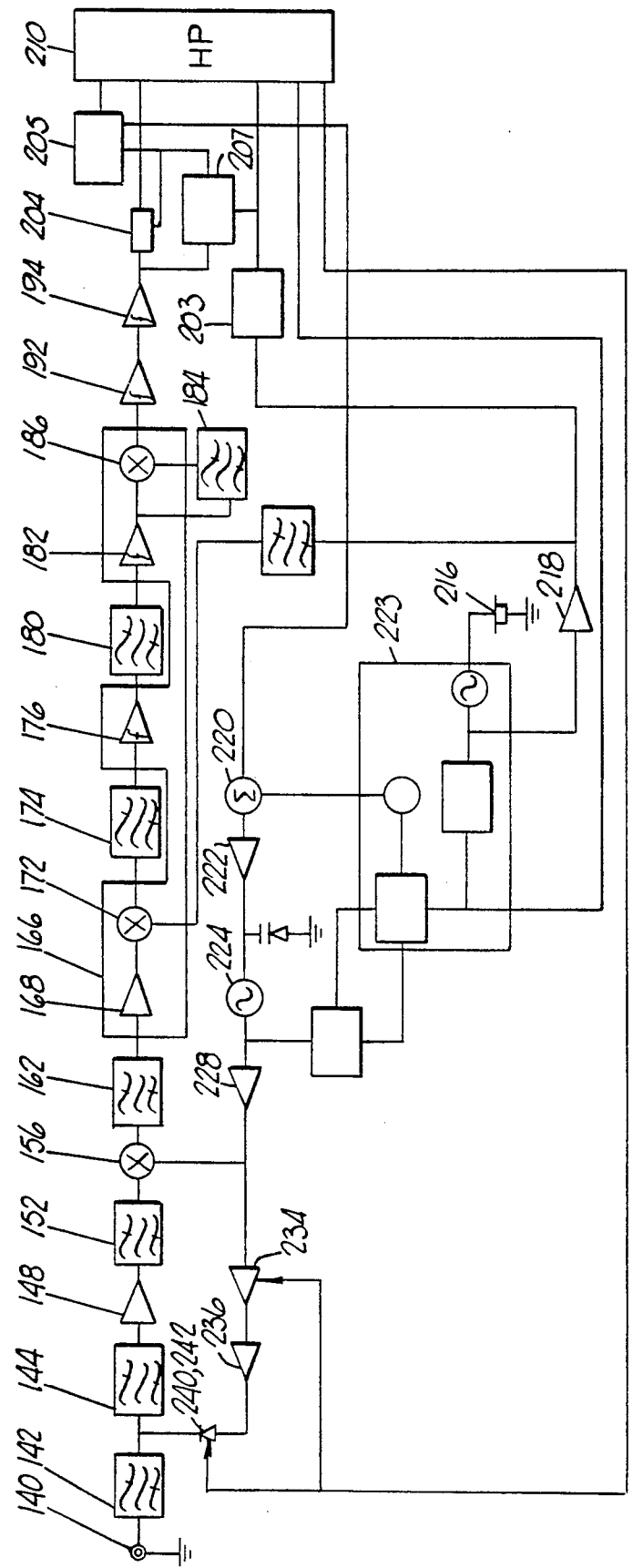
FIG. 1 shows a schematic diagram of the electrical components of the present invention.

An electrical schematic of the transceiver is shown in FIG. 1. This figure represents an overview of the transceiver in that it highlights the macroscopic elements (e.g. mixers, filters, etc.) necessary to process either an incoming or outgoing signal. The following section describes the major individual components of the transceiver.

The antenna 140 serves as the first point for signal reception and the final point for signal transmission. This port in the preferred embodiment is grounded to the RF and DC grounds.

A standard low-pass filter 142 is used to truncate the high frequency energy of the transmitted signal. The cutoff frequency for this filter is approximately 1.16 Hz in the preferred embodiment.

A standard bandpass filter 144 is used only for received signals. It has cutoff frequencies of 902 on the low end and 928 on the high end; the function of the bandpass filter is to eliminate energy from all frequencies outside of this range.

Once the received signal has undergone preliminary filtering, an amplifier 148 is used to increase the signal strength by 17 dB.

A second bandpass filter 152 is used to eliminate energy from all frequencies except for those in the 902 MHz to 928 MHz range.

A mixer 156 is used to convert the incoming signal from the 862 MHz-888 MHz range down to 40.1 MHz. It uses an signal generated by the transmitting synthesizer that is offset from the incoming signal by 40.1 MHz (e.g. if the incoming signal is 880 MHz, it uses a 920.1 MHz ing signal) This "preliminary" mixing is performed in order to minimize aliasing as explained below.

A standard, accurate bandpass intermediate frequency (IF) filter 162, which has cutoff frequencies of 39 MHz on the low end and 41 MHz on the high end, is used to eliminate energy from all frequencies except those near 40.01 MHz.

The FM detector 166 is a standard integrated circuit chip such as a model NEG14 by Signetics, which itself consists of several standard sub-components including limiters, amplifiers, and mixers. The FM detector also provides access points throughout its signal processing path so that the user may enhance or customize the detector to the user's specific needs.

The FM detector amplifier 168 raises the incoming signal strength by 10 dB. The FM detector mixer 172 mixes the 40.1 MHz intermediate frequency down to 10.7 MHz. It uses the third harmonic, 29.4 MHz, of the 9.8 MHz clock source. This harmonic is captured by the FM detector bandpass filter 174 described below.

The FM detector bandpass filter 174, with cutoff frequencies of 10.6 on the low end and 10.7 on the high end, filters the third harmonic, 29.4 MHz of the 9.8 MHz clock source. The circuit taps into one of the FM detector access points to use another standard, accurate If filter to eliminate energy from all frequencies except those near 10.7 MHz.

A FM detector limiter 176 is used in the FM detector in order to remove the amplitude modulation (AM) portion of the signal. This limiter is utilized primarily for "strong" signals.

The circuit again taps into one of the FM detectors access points to use another standard, accurate IF filter 180 to eliminate energy from all frequencies except those near 10.7 MHz.

The remaining three sub-components of the FM detector 166 (limiter 182, filter 184 and mixer 186) are used for quadrature detection. Whereas limiter 176 is used to eliminate the AM component from "strong" signals, limiter 182 is used to remove the AM components from "weak" signals. The output from this limiter is fed to mixer 186 as one input, and a phase delayed output from this limiter (through filter 184) is fed to mixer 186 as a second input. The difference frequency created by mixer 186 is a direct current (DC) voltage that is proportional to the phase difference between the mixer's two inputs.

Slicers 192 and 194 together serve as a window detector: if the incoming frequency is within this "window", the output from slicer 194 is a logical "high"; if the incoming frequency falls outside of this "window", the output from slicer 194 is a logical "low."

The signal output from slicer 194 then feeds into both ripple counter 202 and latch 204. Ripple counter slicer 194 converts the 9.8 MHz clock 206 to a 4.9 MHz clock by dividing the clock signal by two. Ripple counter 202 then converts this 4.9 MHz clock rate to a 76 KHz clock rate by dividing the signal by 64.

A 0 to 1 transition from slicer 194 resets ripple counter 202 which in turn causes the latch to sample the signal from slicer 194. This ensures that the latch will sample the signal in the center of the signal bits time period as explained in more detail below.

It should be noted that ripple counter 202 serves a dual purpose: in addition to providing a clock for latch 204 to use for received signals, the ripple counter also provides clocking for the modular encoder when data is transmitted.

The microprocessor 210 for this invention is a Motorola M6805 running at a clock rate of 4.9 MHz (from ripple counter 203). The microprocessor is used to process received signals, generate transmitted signals, and to serve as an interface for external serial communications via the EIA RS-232 port. The microprocessor also provides control signals (such as frequency control and transmit control) to other portions of the invention. This extremely inexpensive microprocessor can be used instead of a much more expensive microprocessor because of some very unique design features of this invention as explained in more detail below.

Modular encoder 205 component converts the data to be transmitted to the proper format for modulation. This invention uses a dual binary encoding scheme as explained in more detail below. It uses the 76.8 MHz clock generated by ripple counter 202.

The invention uses only one clock source for every function. This highly accurate 9.8 MHz clock 216 is used with various harmonics in conjunction with ripple counters (dividers) and an oscillator to create any needed clocking rate.

Amplifier 218 is used to increase the signal strength of the clock source by 10 dB. An adder 220 sums the signal produced by the phase detector of the synthesizer 223 with the output of modular encoder 205 to produce the signal which will drive oscillator 224. Amplifier 222 is used to increase the signal strength of the output of adder 220 by 22 dB. An oscillator 224 generates a signal in the 902 MHz to 928 MHz range based on the signal input from amplifier 222. Amplifier 228 is used to increase the signal strength of the output of oscillator 224 to +3 dB.

A switched amplifier 234 is used to increase the signal strength of the output of amplifier 228 by 10 dB during signal transmission only. This amplifier is switched off by the microprocessor during signal reception so as not to interfere with the incoming signal.

Amplifier 236 increases the signal strength of the signal of amplifier 234 during transmission by 5 dB. This results in a transmitted signal strength of approximately 17 dB (50 mW).

Switched diodes 240 and 242 are controlled by the microprocessor 210 to allow or disallow signal transmission. During receive mode, these are "shut off" and they are "turned on" during transmission mode.

Next is a description of how the aforementioned components operate. Signal reception is described and signal transmission is then described.

The signal first enters the invention through the antenna 140. Upon entering, the signal passes through low-pass filter 142 in order to eliminate energy from high-frequency noise signals.

The signal is then passed through band-pass filter 144 in order to eliminate energy from low frequency components. The resulting signal is then amplified by amplifier 148 and filtered again by band-pass filter 152 creating a relatively clean signal in the 862 MHz to 888 MHz range. Mixer 156 then uses an offset frequency in the 902 MHz to 928 MHz range in order to create a 40.1 MHz IF signal. This mixing results in an "image" created at the sum and difference of the oscillator frequency and the incoming signal. By first mixing the incoming signal down to 40.1 MHz, this provides greater separation (40.1 MHz) between the signal and its images than it would if it mixed directly to 10.7 MHz (which would only provide 10.7 MHz separation). This greater separation allows IF filter 162 to easily filter out the "images" leaving a clean 40.1 MHz signal. This signal is then amplified by FM detector amplifier 168 and mixed down to 10.7 MHz by mixer 172. Note that mixer 172 uses the third harmonic (29.4MHz) of the solitary 9.8 MHz clock 216 to mix the 40.1 MHz signal to 10.7 MHz. The images from this mixing are then filtered out by band-pass FM detector filter 174. Limiter 176 is then used to eliminate the AM component from this frequency modulated (FM) signal. FM detector band-pass filter 180 cleans-up this signal and feeds it to limiter 182 which is used for weaker signals. The output of limiter 182 travels two separate paths: one path leads directly from limiter 182 to mixer 186 while the second path leads from limiter 182 to mixer 186 via filter 184. The second path through 184 creates a phase-delayed signal which is mixed with the direct signal by mixer 186. This quadrature detector scheme results in an output that is proportional to the incoming frequency. The two slicers, 192 and 194, are then used to create a "window detector." This detector creates a frequency window; if the input to this detector falls within this window, the output is high; if the input to this detector falls outside of this window, the output is low. The output of this slicer, then, is the data which is fed to the microprocessor. However, the serial peripheral interface on the microprocessor which is used to receive and transmit data is not specifically designed with the intent of serving as a signal interface; rather, it is designed to be used with other microprocessors. This invention accommodates the unique signals required by this serial peripheral interface so that it may be used as a signal interface. An essential element of using this serial peripheral interface in this manner is latch 204 which performs the functions of resetting the clock as well as the microprocessor. It should be noted that the latch uses the 9.8 MHz clock signal after it has been divided by 128 (by ripple counters 203 and 202). This portion of the invention will be explained in further detail.

Normally, a very fast microprocessor (e.g. a 30 MHz Motorola MC68000) would be required to adequately process the incoming data on a bit-by-bit basis. Although this invention receives the incoming data on a bit-by-bit basis into the microprocessor's serial shift register, it performs all processing on a byte basis. As a result, a much lower performance and lower cost microprocessor can be used.

Signal transmission begins at the microprocessor 210. Data is shifted out from the microprocessor 210 to modular encoder 205 where it is encoded into a dual binary scheme. At this point, the signal consists of a very broad range of frequencies which have a sin(x)/(x) Fourier transform.

Normally, Manchester encoding is used with FSK signals. Manchester encoding substitutes two bits for each information bit. A "+1/−1" signal might be used to represent a "0" while a "−1/+1" might be used to represent a "1." The purpose of doing this is two-fold: first, it eliminates the DC component of the transmitted signal by alternating the polarity of the transmitted signal bits; second, by providing a data bit value during each clocking cycle, Manchester encoding provides an easy method of deriving the clocking signal at the receiving end.

This invention, however, uses a variation of bipolar encoding instead of Manchester encoding. In bipolar encoding, a "0" signal is used to represent a "0" data bit while alternating polarity "1's" are used to represent a "1" data bit. Over a period of time, the alternating polarity of "1's" effectively eliminates the DC component as does Manchester encoding. For example, an "unencoded" signal of 0111001 might be transmitted as 0, +1, −1, +1, 0, 0, −1. In this way, bipolar encoding eliminates the DC component without doubling the bandwidth required. As a result of this encoding, the output of the modular encoder is a signal which has no DC component, and an insignificant low frequency component as well. The output of the modular encoder is then fed into adder 220 along with the error signal from the synthesizer 223. The modular encoder's signal perturbs oscillator 224 to create a signal in the 902 MHz to 928 MHz range.

The synthesizer 223 used in this invention consists of a phase-locked loop and variable dividers. The phaser locked loop serves two purposes: to center the transmitted signal in the appropriate frequency channel and to switch from one frequency channel to another. The frequency control output of the microprocessor dictates which channel the synthesizer should be using. When the value of the variable divider is changed by the microprocessor 210, a large error voltage is created by the phase locked loop. This large error voltage causes the feedback loop to move the modular encoder's signal into the new frequency channel. Once in the desired channel, the phased locked loop creates small error voltages to maintain the signal of the modular encoder 205 in that frequency channel. Since the synthesizer is used a part of a high-speed data transmission system, the time required to change from one channel to another must be very short otherwise the transmitted signal would be intermittent. The technique used to accomplish this will be described in further detail below.

Amplifier 228 then increases the strength of this synthesized signal which is then either used for mixing during signal reception mode or fed to 234 during signal transmission mode. In transmission mode, amplifier 234 is switched on by the microprocessor and amplifies and relays the incoming signal to amplifier 236. During signal reception mode, it would not be desirable for this generated signal to interfere with the incoming signal so the microprocessor switches off amplifier 234. In transmission mode, amplifier 236 then amplifies the signal to 17 dB (50 mW) for transmission by the antenna 140.

Switched diodes 240 and 242 are used to preclude signal interference during signal reception mode.

In order to provide a high-performance RF communication system, this invention uses some components in non-standard way (such as the serial peripheral interface on the microprocessor), and creative design ideas. Set forth below is some detail on how these features differ from other RF systems.

One aspect of this invention is the method of clocking used for the different components. It should be noted that clocking signals are required for the local oscillator, the IF amplifier (from 40.1 MHz to 10.7 MHz), the modular encoder 205, and for the microprocessor; these components all require different clock rates. Accomplishing this by using multiple clock sources would require significant effort and circuitry to properly synchronize these clocks, and a small difference in clock rates could distort the information contained within the signal. Moreover, using multiple clock sources complicates the circuitry and increases the cost. This invention eliminates these complications by creatively employing one clock source; harmonics of this 9.8 MHz clock are then used to create clocking necessary for all of the aforementioned components.

Another feature of this invention is the use of a relatively low performance and low cost microprocessor 210 for signal processing. The serial peripheral interface (SPI) on the microprocessor is normally used to interface to other microprocessors. This SPI consists of a shift register, a read buffer, and the microprocessor's high speed data bus. Because timing and speed are not critical in microprocessor to microprocessor communication, the SPI is not double buffered. This means that the data coming into the SPI is read in to the shift register one bit at a time. When the shift register is filled, it raised a flag which signals the microprocessor that it is full. Upon seeing this flag raised, the microprocessor waits for the following clock edge and then loads the data from the shift register into the read buffer and then onto its internal data bus. The time required between when the flag is raised and the next clock edge occurs is equal to the time delay required for moving a filled shift register into the microprocessor.

For inter-microprocessor communication, the delay involved in moving the data from the shift register onto the internal data bus is not critical. However, this invention uses the SPI to feed the incoming data to the microprocessor. As such, it is imperative that the data stream into the microprocessor be continuous in order to maximize the efficiency of the microprocessor. For the data stream to be continuous, the time required to move the data from the shift register into the microprocessor must be less than one bit time.

This invention solves this problem by employing an extremely narrow duty cycle clock to the microprocessor. For example, the shift register may contain five bits. The sixth, seventh, and eight bits are shifted into the register on the leading edge of the clock. As soon as the eighth bit is shifted in, the register raises a flag indicating to the microprocessor that it is filled. The microprocessor is almost immediately able to move the data onto its bus because the falling edge of the clock occurs very quickly after the leading edge. This is made possible by using a very narrow duty cycle clock. As a result, the data is moved from the shift register into the microprocessor prior to the next bit arriving.

The above discussion reveals that the microprocessor receives data in eight-bit groups (one byte at a time). The microprocessor then processes the entire byte as a whole rather than each bit individually. This greatly reduces the processing speed required of the microprocessor. As a result, this invention is able to use a relatively low speed and extremely inexpensive microprocessor for its signal processing.

As mentioned above, the serial peripheral interface (SPI) on the microprocessor is normally used to interface to other microprocessors. As such, it requires very specific clocking signals to synchronize itself with the other microprocessor. In this invention, the SPI is used to interface with a data signal.

Normally in a situation like this, a phase-locked loop would be used to continuously derive the clocking signal from the incoming data. However, using such a mechanism would greatly increase the complexity and the cost of the invention. Rather than continuously deriving the clocking signal from the incoming data, this invention uses its own clock source in synchronicity with the incoming data. This is made possible because both the transmitting and receiving portions use a 76 KHz clocking signal which is derived from the extremely accurate 9.8 MHz clock source. Because of this a priori knowledge of the clock rate, this invention is able to synchronize the incoming data signal with the local clock signal just once and be assured that the two will remain in synchronization thereafter. The exact method by which this is accomplished is described below:

Normally, latch 204 is in the "on" state and allows all incoming data to proceed to the microprocessor. As explained above, the microprocessor receives this data and processes it on a byte basis. When transmission is to commence, the transmitting side sends a series of 16 "zeroes". This is done to ensure that the microprocessor on the receiving end will receive at least one full byte of all "zeroes". When the receiving microprocessor sees one full byte of all "zeroes", it resets latch 204 which in turn causes the serial peripheral port on the microprocessor to be deactivated (turned "off"). When latch 204 sees a "one" being received, it turns the serial peripheral interface "on" and resets ripple counter 202 to synchronize the local clock with the incoming signal. This initial "one" is then the first bit to be loaded into the serial peripheral interface's shift register. This can be described by the following example.

The sending side transmits sixteen "zeroes" followed by a "one" in order to signal transmission initiation. Assume the receiving microprocessor loads four bits of noise into its shift register (0101 for example) prior to seeing any of the transmitted sixteen "zeroes." The receiving microprocessor then shifts in the first four of the sixteen "zeroes" to fill its shift register. Since this register does not consist of eight bits of "zero", the microprocessor does not react. However, the next eight bits the microprocessor shifts into its register are the fifth through twelfth "zeroes" which were transmitted. Now seeing a full byte (eight bits) of "zeroes", the microprocessor resets latch 204 which in turn disables the serial peripheral interface on the microprocessor.

Latch 204 then sees the thirteenth through sixteenth "zeroes" which were transmitted but does not pass them on because it is in its "off" state. However, the following "one" causes the latch to switch into its "on" state. As a result, the latch resets ripple counter (203) to synchronize the local clock to this received "one" and also turns "on" the serial peripheral interface. The received "one" is then shifted into the microprocessor shift register and signal reception commences.

As mentioned earlier, the synthesizer (consisting of variable dividers and a phase-locked loop) performs two fundamental function: switching between frequency channels, and maintaining a signal in a given frequency channel.

In order to maintain signal continuity when switching frequency channels, the phase-locked loop must be able to perform this switch as rapidly as possible. This is done by using a phase-locked loop with a very high bandwidth (high cutoff frequency). However, when the signal is to be maintained in a given frequency channel, the bandwidth of the phase-locked loop needs to be as low as possible in order to avoid disturbing the signal from the modular encoder; that is, the cutoff frequency of the phase-locked loop must be lower than the lowest frequency generated by the modular encoder. This is where the encoding scheme comes into play: as described above, signal emanating from the microprocessor contains all frequency components. However, the modular encoder converts this signal to one with no DC or low frequency components. As a result, the cutoff frequency of the phase-locked loop does not interfere with the modular encoder's signal because it is well below the frequency components of the modular encoder's signal.

However, the problem of using a high bandwidth or low bandwidth phase-locked loop still remains. This invention solves this dilemma by employing both schemes. When the frequency control from the microprocessor causes the variable divider to change (in order to switch frequency channels), a large error voltage is created by the phase-locked loop because at that instant, the reference frequency is far from the center frequency of the "new" frequency channel. This large error voltage causes the bandwidth control of the phase-locked loop to raise the loop's bandwidth (cutoff frequency) thereby enabling rapid channel switching. This occurs rapidly enough so as not to interfere with the modular encoder's signal.

Once the channel has switched, the error voltage of the loop decreases since the new reference frequency is close to the center frequency of the new channel. This small error voltage causes the bandwidth (cutoff frequency) of the loop to be lowered to a level below the lowest frequency component of the modular encoder's signal.

What is claimed is:

1. A frequency-hopped packet radio transceiver, comprising:
   an analog signal processing circuit;
   a modular encoder in electrical communication with the analog signal processing circuit for encoding signals for transmission from the transceiver;
   a microprocessor in electrical communication with the analog signal processing circuit for processing signals; and
   a clock, the clock being in electrical communication with and for synchronizing the analog signal processing circuit and the modular encoder.

2. The transceiver of claim 1, wherein the analog signal processing circuit includes an oscillator and an intermediate frequency amplifier, in operative communication with said clock.

3. The transceiver of claim 2, wherein the clock is a 9.8 MHz clock.

4. The transceiver of claim 1, wherein the microprocessor includes a serial peripheral interface with a shift register, a read buffer and a high speed data bus.

5. The transceiver of claim 4, wherein the microprocessor is programmed to move data from the shift register to the high speed data bus at least a byte at a time by accumulating bits in the shift register.

6. The transceiver of claim 5, wherein the microprocessor uses a duty cycle clocking signal that is narrower than one bit.

7. The transceiver of claim 6, wherein the microprocessor has a latch that which deactivates upon the reception of a byte of a predetermined bit sequence, whereby the microprocessor is synchronized with a transmitting device.

8. The transceiver of claim 1, wherein the analog signal processing circuit includes a phase lock loop to switch to and maintain a signal in one of a plurality of predetermined transmission and receiving channels.

9. The transceiver of claim 1, wherein the modular encoder encodes signals with a code including a +1, a −1 and a 0, whereby the +1 and −1 correspond to 1 bits and the 0 corresponds to 0 bits.

10. A method for frequency-hopped packet transmitting, receiving and processing radio signals, comprising:
    designating a first station;
    designating a second station having a microprocessor, an analog signal processing unit, a modular encoder and a clock;
    synchronizing the microprocessor, analog signal processing unit and modular encoder utilizing said clock;
    synchronizing said first station with said second station; and
    transmitting and receiving signals between said first station and said second station.

11. The method of claim 10, wherein said synchronizing step includes transmitting a predetermined synchronization bit sequence from one of said first station and said second station to the other of said first station and second station.

12. The method of claim 10, further comprising encoding the transmitted signals in a code including a +1, a −1 and a 0, so that the DC and low frequency components of the bit stream are minimized.

13. The method of claim 10, wherein the microprocessor includes a serial peripheral interface with a shift register, a read buffer and a high speed data bus, and bit signals are accumulated in the shift register and moved to the data bus at least a byte at a time.

14. The method of claim 13, wherein the microprocessor duty cycle clock is narrower than one bit, so that the signals are transmitted from the shift register to the data bus in less than a bit.

* * * * *